(12) United States Patent
Pitner et al.

(10) Patent No.: US 8,440,869 B2
(45) Date of Patent: May 14, 2013

(54) USE OF IONIC LIQUIDS CONTAINING TRICYANOMETHIDE ANIONS AS SOLVENTS FOR THE EXTRACTION OF ALCOHOLS FROM AQUEOUS SOLUTIONS

(75) Inventors: William-Robert Pitner, Frankfurt (DE); Emil Ferdinand Aust, Mainz (DE); Michael Schulte, Bischofsheim (DE); Uschi Schmid-Grossmann, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 329 days.

(21) Appl. No.: 13/001,857

(22) PCT Filed: May 28, 2009

(86) PCT No.: PCT/EP2009/003820
§ 371 (c)(1), (2), (4) Date: Dec. 29, 2010

(87) PCT Pub. No.: WO2010/000357
PCT Pub. Date: Jan. 7, 2010

(65) Prior Publication Data
US 2011/0112337 A1 May 12, 2011

(30) Foreign Application Priority Data
Jul. 1, 2008 (EP) .................................. 08011845

(51) Int. Cl.
*C07C 29/86* (2006.01)

(52) U.S. Cl.
USPC .......................................... 568/913; 568/918

(58) Field of Classification Search .................. 568/913, 568/918
See application file for complete search history.

(56) References Cited

U.S. PATENT DOCUMENTS

| 4,445,908 A | 5/1984 | Compere et al. |
| 4,568,643 A | 2/1986 | Levy |
| 4,578,525 A | 3/1986 | Brueckner |

FOREIGN PATENT DOCUMENTS

| GB | 2127811 A | 4/1984 |
| WO | 2006021390 A1 | 3/2006 |

OTHER PUBLICATIONS

Chapeaux, Alexandre et al. "Liquid Phase Behavior of Ionic Liquids with Water and 1-Octanol and Modeling of 1-Octanol/Water Partition Coefficients." (Journal of Chemical Engineering Data), Sep. 10, 2007, pp. 2462-2467, vol. 53, No. 10.
Fadeev, Andrei G. and Michael M. Meagher. "Opportunities for ionic liquids in recovery of biofuels." (Chem. Commun.), Jan. 1, 2001, pp. 295-296, No. 3.
World IP Organization. "International Search Report." PCT/EP2009/003820, Applicant: Merck Patent GMBH. Mailed: Jan. 7, 2010.

*Primary Examiner* — Elvis O Price
(74) *Attorney, Agent, or Firm* — Millen, White, Zelano & Branigan, P.C.

(57) ABSTRACT

The invention relates to a method for the liquid-liquid extraction of alcohols from aqueous solutions using at least one ionic liquid containing a tricyanomethide anion as solvent.

15 Claims, 4 Drawing Sheets

Fig. 4

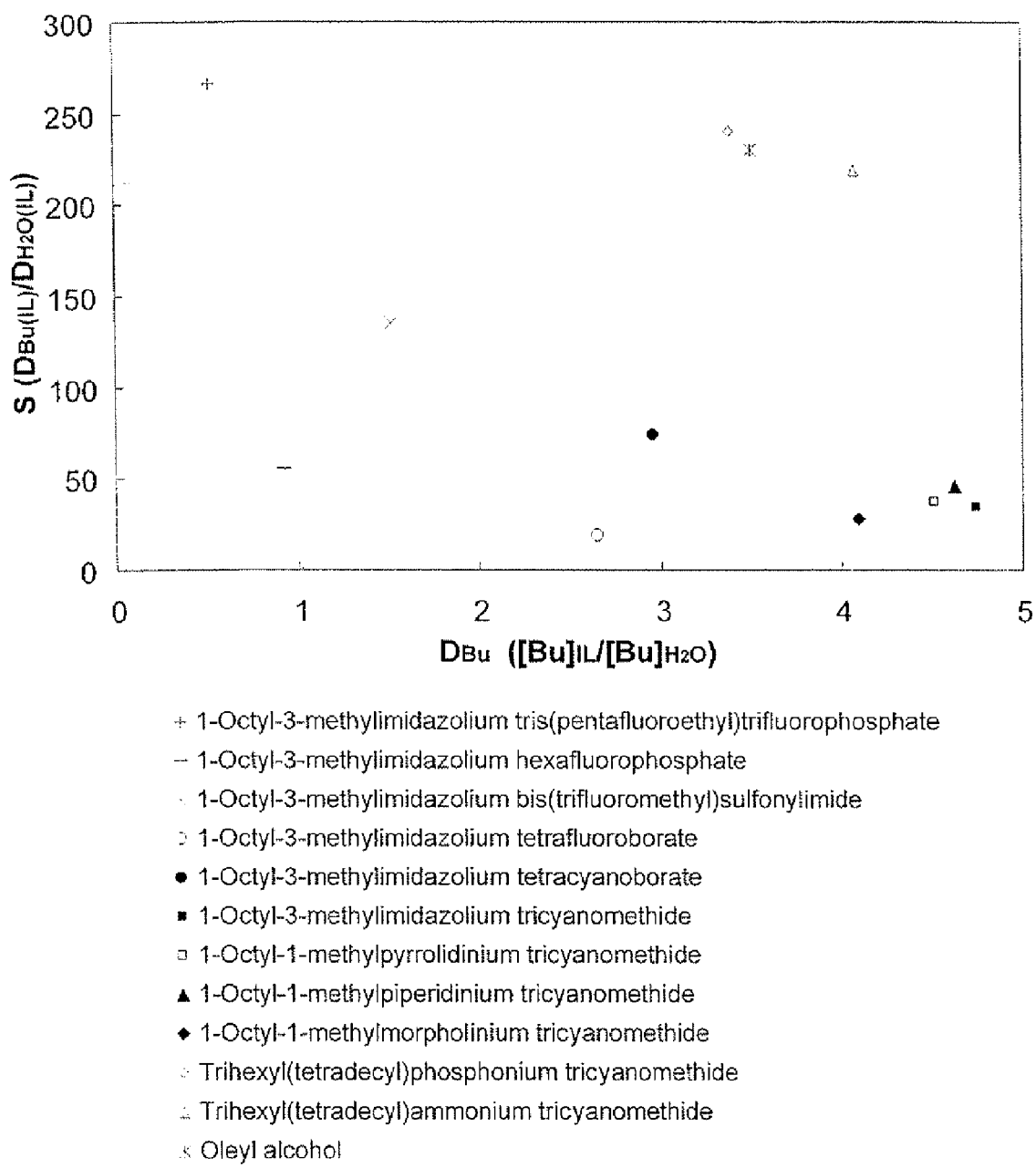

Figure 1:
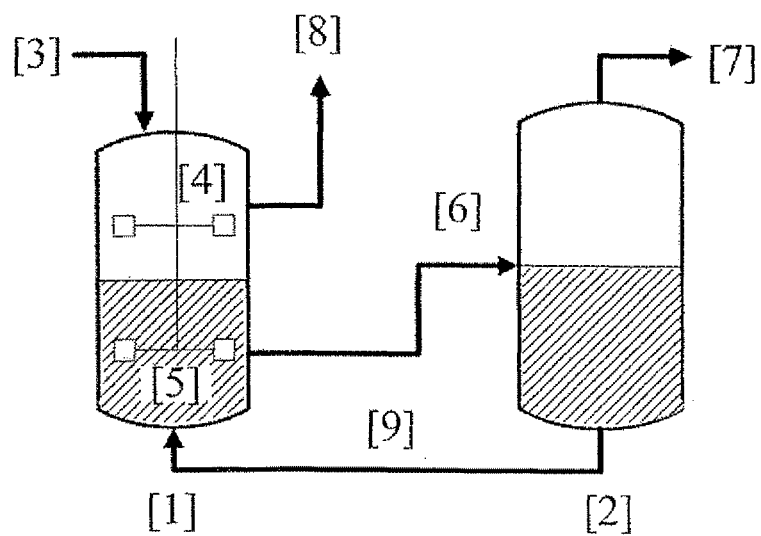

+ 1-Octyl-3-methylimidazolium tris(pentafluoroethyl)trifluorophosphate
− 1-Octyl-3-methylimidazolium hexafluorophosphate
· 1-Octyl-3-methylimidazolium bis(trifluoromethyl)sulfonylimide
○ 1-Octyl-3-methylimidazolium tetrafluoroborate
● 1-Octyl-3-methylimidazolium tetracyanoborate
■ 1-Octyl-3-methylimidazolium tricyanomethide
□ 1-Octyl-1-methylpyrrolidinium tricyanomethide
▲ 1-Octyl-1-methylpiperidinium tricyanomethide
◆ 1-Octyl-1-methylmorpholinium tricyanomethide
◇ Trihexyl(tetradecyl)phosphonium tricyanomethide
△ Trihexyl(tetradecyl)ammonium tricyanomethide
× Oleyl alcohol

USE OF IONIC LIQUIDS CONTAINING TRICYANOMETHIDE ANIONS AS SOLVENTS FOR THE EXTRACTION OF ALCOHOLS FROM AQUEOUS SOLUTIONS

The invention relates to a method for the liquid-liquid extraction of alcohols from aqueous solutions using at least one ionic liquid containing a tricyanomethide anion as solvent.

The extraction of alcohols from aqueous solutions is increasing more and more in importance due to intense debate about "white biotechnology" or the use of alcohols as additives to conventional fuels. As part of the intense debate about biofuels, in particular bioethanol, it has emerged that biobutanol, i.e. butanol prepared from biomass, is likewise of interest as potential biofuel.

Biobutanol has a number of advantages over other biofuels, in particular
owing to the low vapour pressure (5.6 hPa compared with 58.5 hPa in the case of ethanol) and the relatively low flash point (36° C. compared with 12° C. for ethanol), it can easily be mixed with conventional fuels,
it exhibits significantly less hygroscopic behaviour,
the energy content is similar to that of conventional fuels,
it is, for example, less corrosive,
it can replace fossil fuels to the extent of 100% without the need for engine modifications and
it can be mixed with biodiesel/diesel and used in diesel engines.

The preparation of alcohols from biomass has been known for some time. A fermentation which was already employed industrially in the first half of the twentieth century is ABE fermentation (acetone-butanol-ethanol fermentation). At that time, the microorganism *Clostridium acetobutyricum* was employed. Nowadays, further bacteria from the *Clostridium genus*, such as, for example, *C. beijerinckii, C. saccharoperbutylacetonicum* and *C. tetanomorphum*, are employed for the preparation of butanol from biomass. In addition, new microorganisms, in particular bacteria and yeasts, are being developed which produce a higher butanol proportion and in addition are also more tolerant to butanol in the fermentation solution. However, the tolerance limit is as low as 2 percent by weight of butanol, based on the aqueous solution.

The extraction of alcohols, in particular butanol, from an aqueous solution, and in a particular embodiment the purification of fermentation broths, therefore continues to be a challenge. The removal of alcohols from aquenus solutions by distillation is expensive. Owing to the higher boiling point of butanol compared with water, rectification cannot be carried out economically as a separation method for butanol. Extraction methods used to date require extraction media which are generally flammable, environmentally harmful or toxic.

For the extraction of alcohols from fermentation broths, the fatty alcohol oleyl alcohol is currently being investigated the most frequently. However, this has the disadvantage of being an emulsifier, which may result in foaming on use in liquid-liquid extraction. The formation of a foam phase results in a greater loss of pressure in extraction columns and in addition makes phase separation of the two liquid phases more difficult. In addition, oleyl alcohol is classified as "irritating to respiratory system".

There is therefore a demand for novel extraction media for the extraction of alcohols from aqueous solutions which can be employed as an alternative to conventional compounds and which have a high distribution coefficient and high selectivity for the alcohol to be extracted. The requirements of the novel media are therefore:
good selectivity for the uptake of the alcohol to be extracted, ideally having a selectivity coefficient >100,
good distribution coefficient, for example having a distribution coefficient $D_{alcohol} > 2$,
immiscible with water,
low water uptake by the aqueous solution,
non-toxic to the microorganism if the aqueous solution is a fermentation broth.

The object of the present invention is accordingly to provide novel extraction media for the liquid-liquid extraction of alcohols from aqueous solutions.

This object is achieved in accordance with the invention by the features of the main claim and the co-ordinate claims.

Surprisingly, it has been found that ionic liquids containing tricyanomethide anions are particularly suitable as solvents for liquid-liquid extraction of this type of alcohols from aqueous solutions.

The invention therefore relates to a method for the liquid-liquid extraction of alcohols from aqueous solutions using at least one ionic liquid containing tricyanomethide anions as solvent.

The ionic liquid containing tricyanomethide anions ideally has the property of forming a two-phase mixture with the aqueous solution comprising at least one alcohol.

The invention therefore furthermore relates to a method for the liquid-liquid extraction of alcohols from aqueous solutions using at least one ionic liquid containing a tricyanomethide anion as solvent, characterised in that the ionic liquid containing tricyanomethide anions forms at least one two-phase mixture with the aqueous solution comprising at least one alcohol.

The ionic liquids containing tricyanomethide anions and the preparation and uses thereof as solvents for many synthetic or catalytic reactions are known and some compounds are commercially available, Lonza Ltd., Switzerland.

The method according to the invention is a liquid-liquid extraction. In liquid-liquid extraction, in which two liquid phases are involved, the valuable product, in this case the alcohol, is transferred from the support phase into the extract phase. A phase equilibrium with respect to the concentration of valuable product becomes established between the two phases in accordance with the Nernst distribution law:

$$D_{alcohol} = \frac{C_{alcohol}^{IL}}{C_{alcohol}^{AQ}}$$

$D_{alcohol}$=Nernst distribution coefficient for the valuable product, here alcohol
$C_{alcohol}^{IL}$: concentration of the valuable product, here alcohol, in the ionic liquid
$C_{alcohol}^{AQ}$: concentration of the valuable product, here alcohol, in the aqueous phase
The selectivity S is defined as the quotient of the Nernst distribution coefficients of alcohol to water:

$$S = \frac{D_{alcohol}}{D_{water}}$$

Liquid-liquid extraction is a separation method in which mass transfer takes place between two liquid phases and is limited by the thermodynamic equilibrium that becomes established, in accordance with the Nernst distribution coefficient.

The liquid-liquid extraction according to the invention of alcohols from aqueous solutions using at least one ionic liquid containing tricyanomethide anions is preferably carried out by a method in which a) the aqueous solution comprising at least one alcohol is provided, b) the aqueous solution from a) is mixed intensively with the at least one ionic liquid containing tricyanomethide anions, so that the ionic liquid is able to extract at least some of the alcohol from the aqueous solution and form an at least single-phase mixture with this alcohol, c) the at least single-phase mixture from b) is separated off from the aqueous solution, d) the single-phase mixture from b) is separated into the components alcohol and ionic liquid, and optionally e) the ionic liquid from d) is fed back into step b).

The liquid-liquid extraction according to the invention, as described, can be carried out by the batch method. However, it can also be carried out continuously or semi-continuously. The liquid-liquid extraction here can be carried out by either the countercurrent, co-current or cross-current method and in one or more steps. The liquid-liquid extraction can be carried out either in a one-step or multistep mixer-settler battery or alternatively in an extraction column. The method according to the invention can be carried out in all extraction apparatuses and by all procedures known to the person skilled in the art, for example documented by the specialist literature by J. Rydberg, M. Cox, C. Muskas, G. R. Chopppin, 2004, Solvent Extraction Principles and Practice or R. H. Perry, 1984, Perry's chemical engineer's handbook.

A variant of a liquid-liquid extraction is described in FIG. 1.

The reference numbers in FIG. 1 are as follows:

[1] Reaction vessel containing the aqueous solution comprising at least one alcohol and the ionic liquid according to the invention, in particular an in-situ fermenter

[2] Recovery unit

[3] Addition of the aqueous solution comprising at least one alcohol, in particular the fermentation medium including microorganisms and ionic liquid

[4] Aqueous phase of the aqueous solution comprising at least one alcohol, in particular in the case of fermentation also the microorganisms

[5] Ionic liquid phase, optionally comprising the part of the extracted alcohol forming the at least single-phase mixture

[6] Stream to the recovery unit comprising the ionic liquid phase comprising the part of the extracted alcohol

[7] Extracted and separated-off alcohol

[8] Optionally discharged stream of the aqueous phase, in particular the fermentation broth

[9] Return of the purified ionic liquid.

In [1], the aqueous phase comprising the at least one alcohol, in particular the fermentation broth comprising fermentation medium and microorganisms, is brought into contact and mixed with the ionic liquid. In the case of the preferred embodiment of fermentation, the fermentation, i.e. the production of the alcohol by the microorganisms, and separation of the alcohol from the fermentation broth by extraction by means of an ionic liquid take place simultaneously in [1]. After separation of the phases in [4] and [5], the ionic liquid is fed into a recovery unit [2] by means of stream [6], and the butanol is separated off and discharged in stream [7]. The regenerated ionic liquid is fed back into [1] in stream [9].

Figure 2:
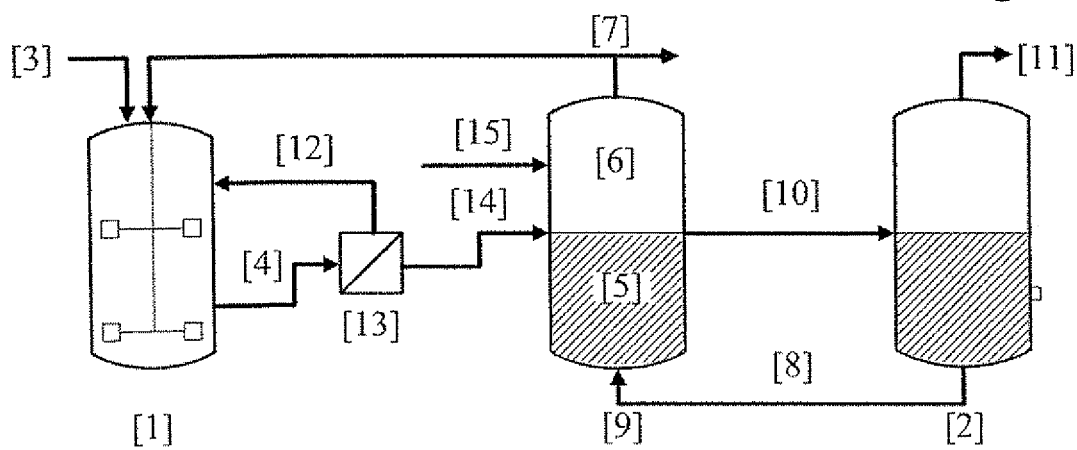

A variant of a fermentation according to the invention with the aid of an extraction column is described in FIG. 2.

The reference numbers in FIG. 2 are as follows:

[1] Fermenter

[2] Recovery unit

[3] Addition of the fermentation medium including microorganisms

[4] Fermentation broth

[5] Ionic liquid phase, optionally comprising the extracted alcohol part forming the at least single-phase mixture

[6] Aqueous phase of the aqueous solution comprising at least one alcohol

[7] Discharged aqueous phase, which may also be fed back into [1]

[8] Optionally discharged stream of the aqueous phase, fermentation broth

[9] Extraction column

[10] Stream to the recovery unit comprising the ionic liquid phase comprising the extracted alcohol part

[11] Extracted and separated-off alcohol

[12] Cell return stream, comprising the microorganisms and in some cases fermentation medium

[13] Cell separation unit

[14] Aqueous phase of the aqueous solution comprising at least one alcohol

[15] Addition of the ionic liquid

The fermentation broth comprising fermentation medium and microorganisms is stirred and aerated in [1]. Part of the fermentation broth is fed to the cell separation unit by means of stream [4]. The cells or microorganisms are separated in the cell separation unit [13]. The cells or microorganisms are returned to the fermenter [1] by means of stream [12]. The separated-off aqueous solution comprising at least one alcohol is fed into the extraction column [9] by means of stream [14]. The two phases, aqueous phase comprising at least one alcohol and ionic liquid optionally comprising the part of the extracted alcohol, are brought into contact in the extraction column [9]. The alcohol is extracted in the extraction column, i.e. part thereof is transferred from the aqueous phase into the ionic liquid phase. The aqueous phase is removed semi-continuously in stream [7], and some or all thereof is fed back into [1]. The ionic liquid phase comprising the part of the extracted alcohol is fed into a recovery unit by means of stream [10]. The alcohol is separated off from the ionic liquid in the recovery unit [2] and discharged in stream [11]. The regenerated stream [8], the regenerated ionic liquid comprising no alcohol, is fed back into the extraction column [9].

In general, the term alcohol in the sense of the invention encompasses both monohydroxyalcohols, preferably having 2, 3 or 4 C atoms, and alcohols containing more than one hydroxyl group, for example diols, preferably having 3, 4 or 5 C atoms.

Selected diols are, for example, 2,3-butanediol and 1,3-propanediol.

In a preferred embodiment of the invention, the at least one alcohol is selected from the group ethanol, isopropanol, propanol, n-butanol or isomers of n-butanol, or mixtures thereof. The method according to the invention is particularly preferably used for the extraction of n-butanol, isomers of n-butanol or mixtures thereof.

The so-called biobutanol prepared by fermentation comprises n-butanol as principal component and isomeric butanols as secondary constituents. The term n-butanol is equivalent to 1-butanol.

The aqueous solution in the method according to the invention comprises the alcohol in a concentration of 0.01 to 50 percent by weight, preferably in a concentration of 0.1 to 30 percent by weight, particularly preferably in a concentration of 0.5 to 10 percent by weight, based on the aqueous solution. For aqueous solutions from biomass, i.e. for fermentation broths, the alcohol is present in a concentration of 0.1 to 3 percent by weight, preferably in a concentration of 0.5 to 2 percent by weight, based on the fermentation broth. A natural limit is the production limit of the microorganism. However, it is also possible to concentrate the fermentation broth in advance and then to carry out the method according to the invention.

In a preferred embodiment of the invention, the aqueous solution comprising at least one alcohol is a fermentation broth, in particular a fermentation broth from an acetone-butanol-ethanol fermentation (ABE fermentation).

For ABE fermentation, the microorganism *Clostridium beijerinckii* used initially has been further developed into *Clostridium beijerinckii* BA101, which is able to produce or tolerate a butanol concentration of up to 17.8 g/l, which is more favourable compared with defined nutrient media, for example glucose corn steep liquor medium. The concentration of the glucose corn steep liquor medium is 60 g/l. Important by-products in this fermentation are acetone and ethanol with concentrations of 5.5 g/l and 1 g/l respectively. Further by-products having very low concentrations are acetic acid and butyric acid.

General expert knowledge includes the temperature at which the liquid-liquid extraction according to the invention is carried out. In the case of the particular embodiment of the extraction of the alcohol from an in-situ fermentation, as defined below, the ideal temperature of the microorganism at which the production of the alcohol can preferably take place should, for example, be noted.

In a preferred embodiment of the present invention, the cation of the ionic liquid containing tricyanomethide anions is hydrophobic.

The cations are preferably organic cations and particularly preferably the organic cations selected from the group comprising ammonium, phosphonium, sulfonium, uronium, thiouronium, guanidinium cations or heterocyclic cations.

From the group of the ammonium, phosphonium or sulfonium tricyanomethides, preference is given to the compounds of the formula (1), (2) or (3):

$$[NR_4]^+[C(CN)_3]^- \quad (1),$$

$$[PR_4]^+[C(CN)_3]^- \quad (2),$$

$$[SR_3]^+[C(CN)_3]^- \quad (3),$$

where
R in each case, independently of one another, denotes
a straight-chain or branched alkyl having 1-20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 5-7 C atoms, which may be substituted by alkyl groups having 1-6 C atoms, with the proviso that at least two substituents R have at least 5 C atoms.

From the group of the uronium or thiouronium tricyanomethides, preference is given to the compounds of the formula (4) or (5):

$$[C(NR^3R^4)(OR^5)(NR^6R^7)]^+[C(CN)_3]^- \quad (4),$$

$$[C(NR^3R^4)(SR^5)(NR^8R^7)]^+[C(CN)_3]^- \quad (5),$$

where
$R^3$ to $R^7$ each, independently of one another, denote
H, where H is excluded for $R^5$,
a straight-chain or branched alkyl having 1 to 20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 3-7 C atoms, which may be substituted by alkyl groups having 1-6 C atoms.

From the group of the guanidinium tricyanomethides, preference is given to the compounds of the formula (6)

$$[C(NR^8R^9)(NR^{10}R^{11})(NR^{12}R^{13})]^+[C(CN)_3]^- \quad (6)$$

where
$R^8$ to $R^{13}$ each, independently of one another, denote
H,
a straight-chain or branched alkyl having 1 to 20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 3-7 C atoms, which may be substituted by alkyl groups having 1-6 C atoms.

From the group of the tricyanomethides containing a heterocyclic cation, preference is given to the compounds of the formula (7)

$$[HetN]^{z+}[C(CN)_3]^-_z \quad (7),$$

where
$HetN^{z+}$ denotes a heterocyclic cation selected from the group

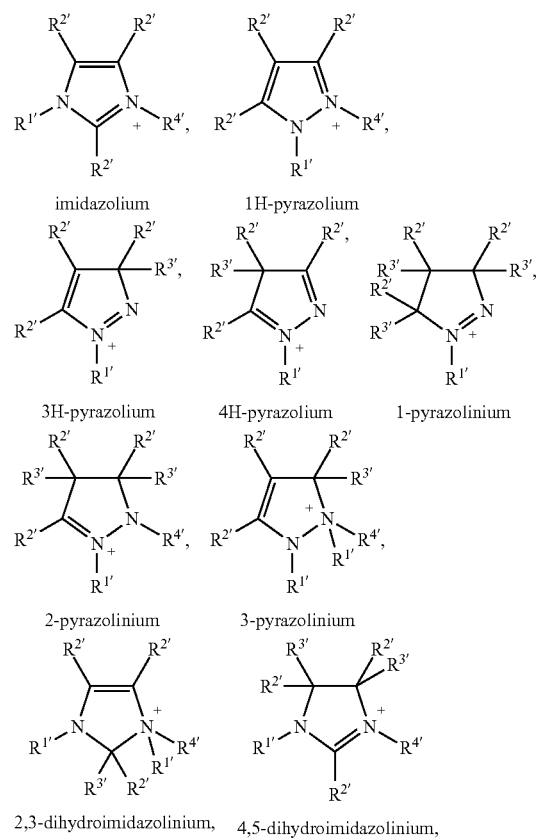

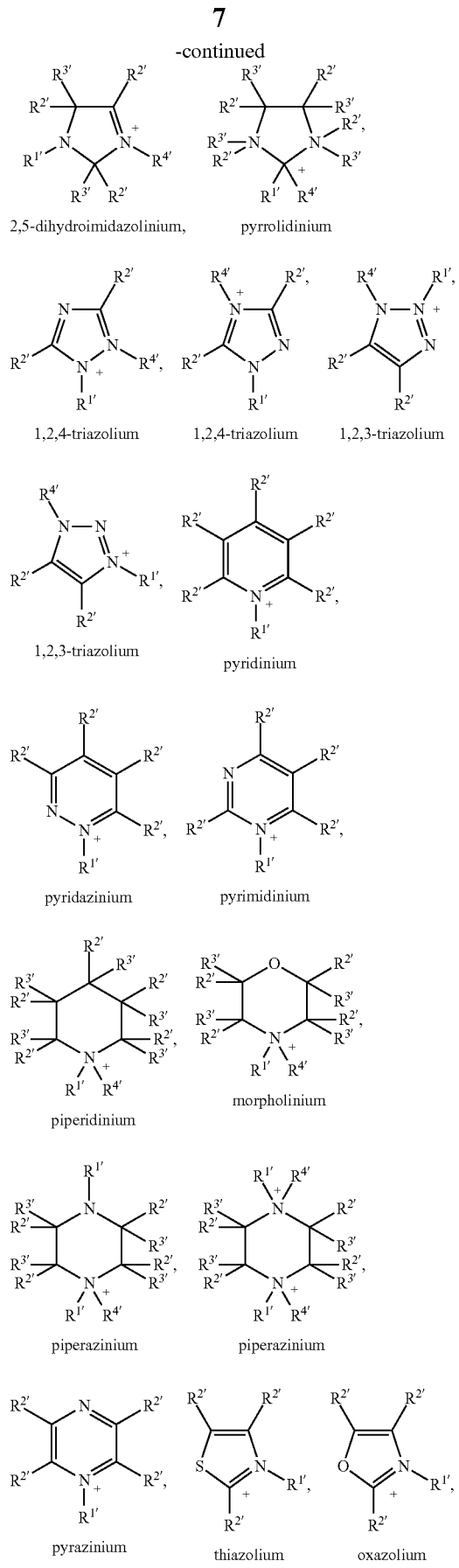
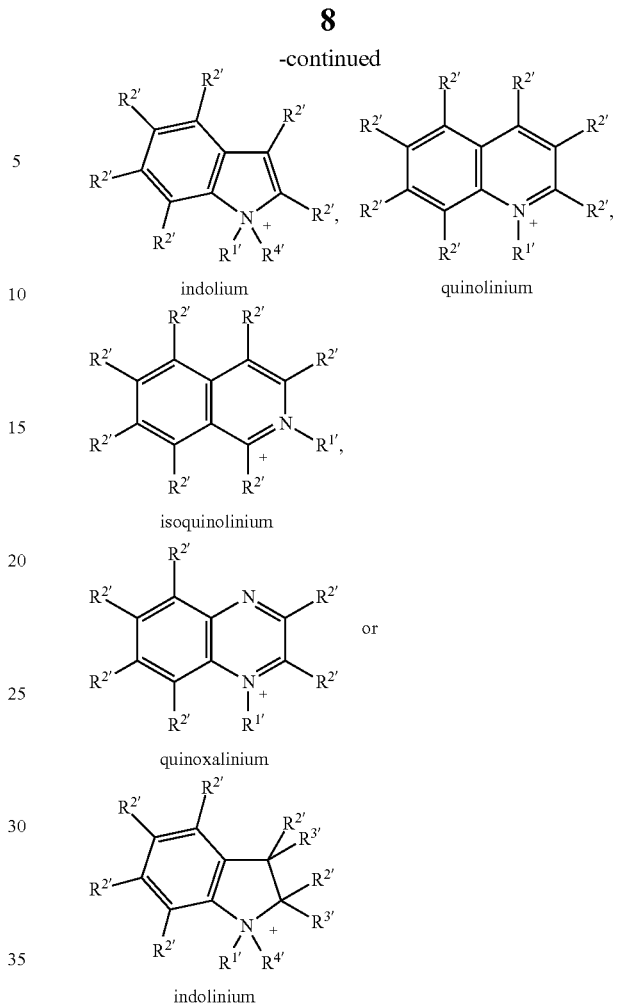

where the substituents $R^{1'}$ to $R^{4'}$ each, independently of one another, denote a straight-chain or branched alkyl having 1-20 C atoms, a straight-chain or branched alkenyl having 2-20 C atoms and one or more double bonds, a straight-chain or branched alkynyl having 2-20 C atoms and one or more triple bonds, saturated, partially or fully unsaturated cycloalkyl having 5-7 C atoms, which may be substituted by alkyl groups having 1-6 C atoms, where the substituents $R^{1'}$, $R^{2'}$, $R^{3'}$ and/or $R^{4'}$ together may also form a ring system.

For the purposes of the present invention, fully unsaturated substituents are also taken to mean aromatic substituents.

In accordance with the invention, suitable substituents R and $R^3$ to $R^{13}$ of the compounds of the formulae (1) to (6) are in each case, independently of one another, preferably $C_6$- to $C_{18}$-, in particular $C_8$- to $C_{14}$-alkyl groups.

The substituents R in the compounds of the formula (1), (2) or (3) may be identical or different. For ammonium or phosphonium tricyanomethides of the formula (1) or (2), three substituents R are preferably identical and one substituent R is different. For the sulfonium tricyanomethides of the formula (3), two substituents R are preferably identical and one substituent R is different.

The substituents R are particularly preferably pentyl, hexyl, octyl, decyl, dodecyl or tetradecyl.

Up to four substituents of the guanidinium cation [C(NR$^8$R$^9$)(NR$^{10}$R$^{11}$)(NR$^{12}$R$^{13}$)]$^+$ may also be bonded in pairs in such a way that mono-, bi- or polycyclic cations are formed.

Without restricting generality, examples of such guanidinium cations are:

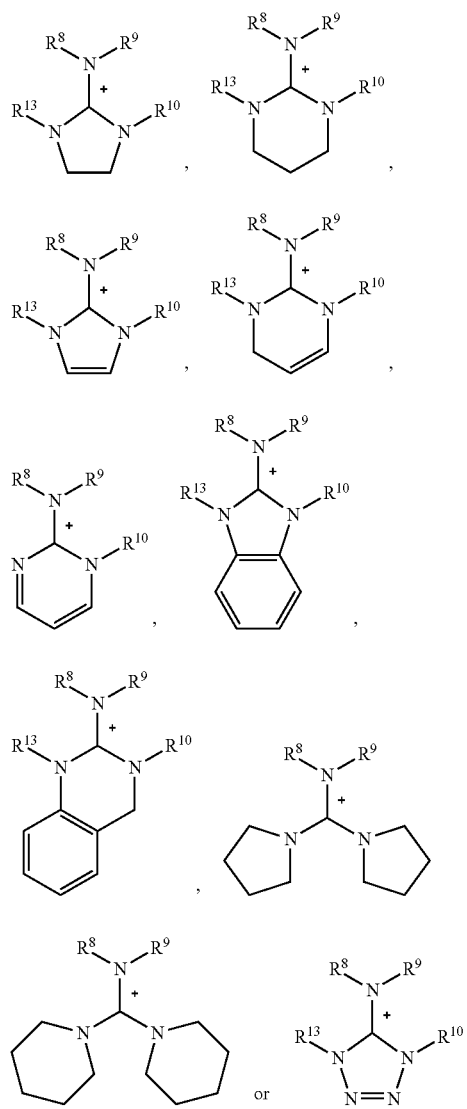

where the substituents R$^8$ to R$^{10}$ and R$^{13}$ can have a meaning indicated above or a particularly preferred meaning.

If desired, the carbocycles or heterocycles of the guanidinium cations indicated above may also be substituted by C$_1$- to C$_6$-alkyl.

Up to four substituents of the uronium cation [C(NR$^3$R$^4$)(OR$^5$)(NR$^8$R$^7$)]$^+$ or thiouronium cation [C(NR$^3$R$^4$)(SR$^5$)(NR$^8$R$^7$)]$^+$ may also be bonded in pairs in such a way that mono-, bi- or polycyclic cations are formed.

Without restricting generality, examples of such cations are indicated below, where Y=O or S:

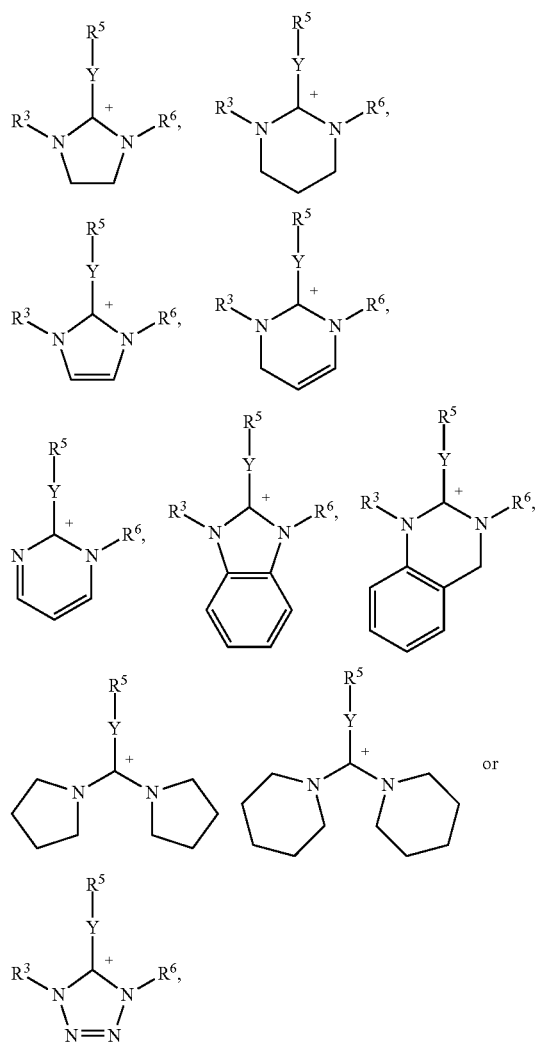

where the substituents R$^3$, R$^5$ and R$^6$ can have a meaning indicated above or a particularly preferred meaning.

If desired, the carbocycles or heterocycles of the cations indicated above may also be substituted by C$_1$- to C$_6$-alkyl.

The substituents R$^3$ to R$^{13}$ are each, independently of one another, preferably a straight-chain or branched alkyl group having 1 to 16 C atoms. The substituents R$^3$ and R$^4$, R$^6$ and R$^7$, R$^8$ and R$^9$, R$^{10}$ and R$^{11}$ and R$^{12}$ and R$^{13}$ in compounds of the formulae (4) to (6) may be identical or different. R$^3$ to R$^{13}$ are particularly preferably each, independently of one another, methyl, ethyl, n-propyl, isopropyl, n-butyl, tert-butyl, sec-butyl, phenyl, hexyl or cyclohexyl, very particularly preferably methyl, ethyl, n-propyl, isopropyl, n-butyl or hexyl.

In accordance with the invention, suitable substituents R$^{1'}$ to R$^{4'}$ of compounds of the formula (7), besides H, are preferably: C$_1$- to C$_{20}$-, in particular C$_1$- to C$_{12}$-alkyl groups.

The substituents R$^{1'}$ and R$^{4'}$ are each, independently of one another, particularly preferably methyl, ethyl, isopropyl, propyl, butyl, sec-butyl, tert-butyl, pentyl, hexyl, octyl, decyl, dodecyl, cyclohexyl, phenyl or benzyl. They are very particularly preferably methyl, octyl, decyl or dodecyl. In pyrrolidinium, piperidinium or morpholinium compounds, the two substituents and R⁴' are preferably different.

The substituent R²' or R³' is in each case, independently of one another, in particular, H, methyl, ethyl, isopropyl, propyl, butyl, sec-butyl, tert-butyl, cyclohexyl, phenyl or benzyl. R²' is particularly preferably H, methyl, ethyl, isopropyl, propyl, butyl or sec-butyl. R²' and R³' are very particularly preferably H.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, iso-pentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Unsubstituted saturated or partially or fully unsaturated cycloalkyl groups having 5-7 C atoms are therefore cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups.

HetN$^{z+}$ is preferably

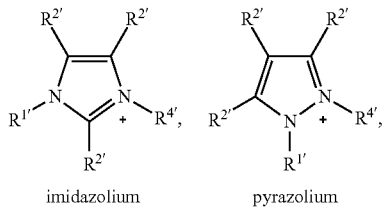

imidazolium          pyrazolium

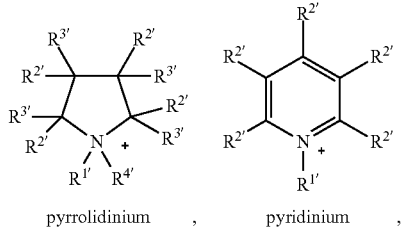

pyrrolidinium    ,    pyridinium    ,

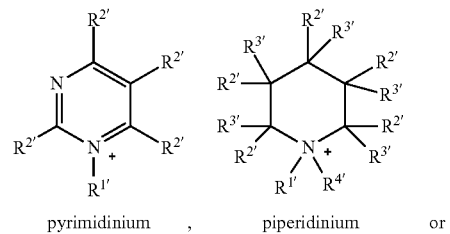

pyrimidinium    ,    piperidinium    or

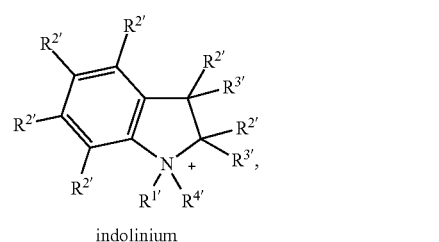

indolinium where the substituents R¹' to R⁴' each, independently of one another, have a meaning described above.

HetN$^{z+}$ is particularly preferably

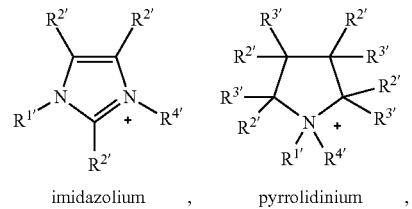

imidazolium    ,    pyrrolidinium    ,

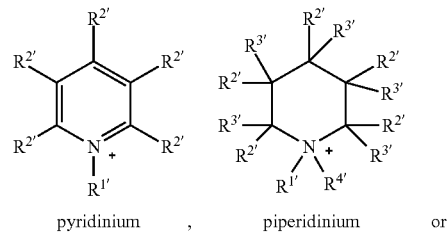

pyridinium    ,    piperidinium    or

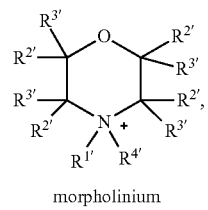

morpholinium where the substituents R¹' to R⁴' each, independently of one another, have a meaning described above.

HetN$^{z+}$ is very particularly preferably imidazolium

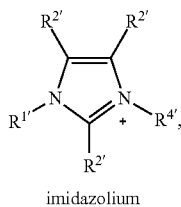

imidazolium where the substituents R$^{1'}$ to R$^{4'}$ each, independently of one another, have a meaning described above.

In a preferred embodiment of the method, the at least one ionic liquid containing tricyanomethide anions is selected from the group of the compounds of the formulae (1), (2) and (7), having substituents as defined or preferably defined above. Very particular preference is given to the use of compounds of the formulae (1) and (2) and preferred compounds thereof, as described above.

The ionic liquids containing tricyanomethide anions for use in the method according to the invention are particularly preferably selected from the group
1-octyl-3-methylimidazolium tricyanomethide,
1-decyl-3-methylimidazolium tricyanomethide,
1-dodecyl-3-methylimidazolium tricyanomethide,
trihexyltetradecylammonium tricyanomethide,
trihexyltetradecylphosphonium tricyanomethide,
N-octylpyridinium tricyanomethide,
1-octyl-1-methylpyrrolidinium tricyanomethide,
N-octyl-N-methylmorpholinium tricyanomethide,
1-octyl-1-methylpiperidinium tricyanomethide.

With respect to the selectivity, very particular preference is given to the ionic liquids of the formulae (1) and (2), as defined or described as preferred above, particularly preferably trihexyltetradecylphosphonium tricyanomethide or trihexyltetradecylammonium tricyanomethide. The selectivities to butanol are, in particular for the individual compounds mentioned, comparable to the selectivity of oleyl alcohol. Further general statements in this respect are also present in the example part.

It goes without saying to the person skilled in the art that substituents, such as, for example, C, H, N, O, Cl, F, in the compounds according to the invention can be replaced by the corresponding isotopes.

The provision of the aqueous solution comprising at least one alcohol in the method according to the invention is part of general expert knowledge. It is possible either to prepare the aqueous solution specifically or to employ an aqueous solution from a production process. In the particular case of the fermentation broth, the production process is a fermentation.

Intensive mixing can preferably be carried out with stirring. However, all other types of mixing are also possible, for example physical processes, such as shaking or ultrasound.

The separation of the at least single-phase mixture from step b) of the method according to the invention from the aqueous solution is carried out by methods which are known to the person skilled in the art.

If the method according to the invention is used in batch operation, separation of the aqueous solution from the at least single-phase mixture comprising at least some of the alcohol to be extracted, as defined above, occurs after completion of the stirring, and the at least one ionic liquid and the lower phase can be separated off, for example, by removal at the bottom of the reaction vessel.

In the case of continuous use of the method, some of the lower phase is likewise taken off continuously at the bottom of the reaction vessel. Reference is made, in particular, to the expert knowledge documented by, for example, the specialist literature by J. Rydberg, M. Cox, C. Muskas, G. R. Chopppin, 2004, Solvent Extraction Principles and Practice or R. H. Perry, 1984, Perry's chemical engineer's handbook.

The upper phase in this separation process is generally the at least multi-phase mixture of the at least one ionic liquid with the extracted part of the alcohol, as described above.

The alcohol component is separated off from the ionic liquid by methods which are known to the person skilled in the art, for example by distillation of the alcohol, stripping, flash, evaporation, adsorption or chromatographic methods.

The treated ionic liquid, as described above, can optionally be fed back into the method according to the invention and is available again as solvent.

The method according to the invention for liquid-liquid extraction can be carried out in continuous, but also in semi-continuous operation, as described above. The purification of the liquid-liquid extraction can be carried out both in situ and also decoupled. The in-situ extraction involves simultaneous fermentation and separation-off of the valuable product, here in accordance with the invention at least one alcohol, as described above, by bringing the fermentation broth into direct contact with the ionic liquid. The valuable product is thus removed from the aqueous phase, and the concentration of the valuable product is kept low, so that it does not inhibit the microorganisms. Inhibition means that the growth of the microorganisms is slowed or even stopped, also causing production of the valuable product to be slowed or even stopped.

The method according to the invention, as described above, can be carried out in any suitable apparatus, as are known to the person skilled in the art.

The invention likewise relates to the use of at least one ionic liquid containing tricyanomethide anions as solvent for a liquid-liquid extraction of alcohols from aqueous solutions.

All comments regarding the preferred embodiments of the method of liquid-liquid extraction, the aqueous solution, the alcohol and the at least one ionic liquid likewise apply to this subject-matter of the invention.

Preferred feature combinations of the invention are disclosed in the claims.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

The ionic liquids containing tricyanomethide anions can be synthesised, for example, in accordance with the disclosure of WO 2006/021390 or the ionic liquids are commercially available.

Examples of the synthesis of selected compounds are:

Example A

Synthesis of trihexyltetradecylammonium tricyanomethide

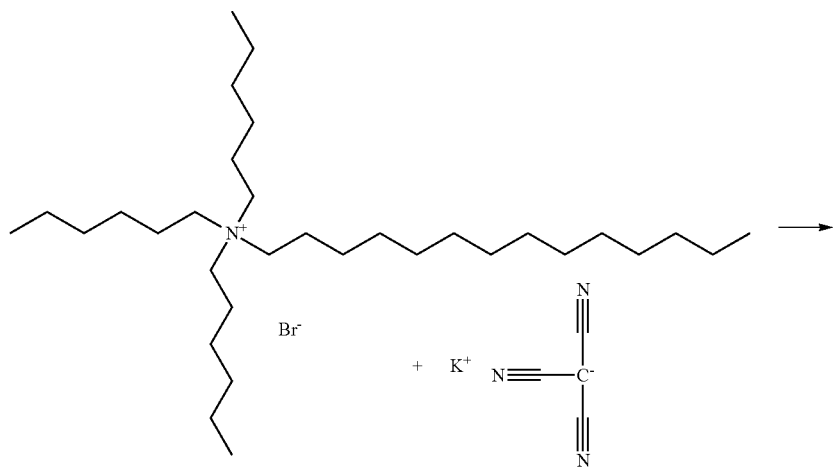

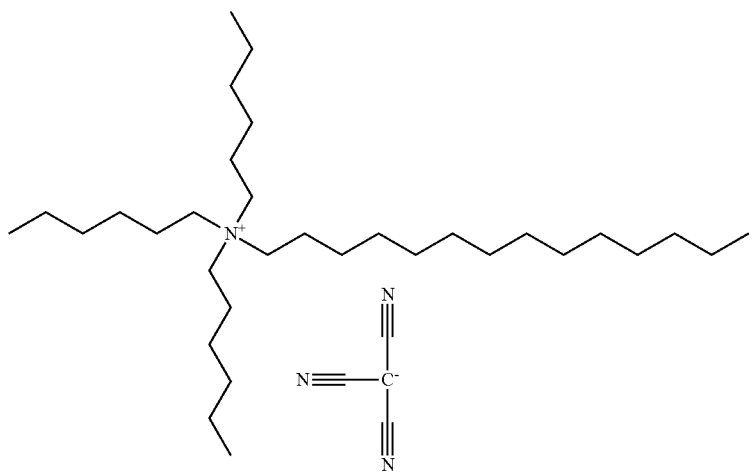

100 g of trihexyltetradecylammonium bromide are dissolved in 400 l of demineralised water, and 26 g of potassium tricyanomethide are subsequently added slowly. This reaction mixture is stirred at room temperature for a further 2 hours (h) and left to stand overnight.

The work-up is carried out by extraction with dichloromethane. The organic phase is then washed free of bromide using demineralised water. 8 g of ALOX and 5 g of activated carbon are added to the organic solution, which is then filtered and subsequently evaporated in a rotary evaporator with a water bath at about 80° C.

1H NMR (d6-DMSO): δ=3.1 (m, 6H), 2.51 (m, 2H), 1.58 (m, 8H), 1.30 (m, 24H), 1.26 (m, 16H), 0.89 (m, 12H).

Example B

Synthesis of trihexyltetradecylphosphonium tricyanomethide

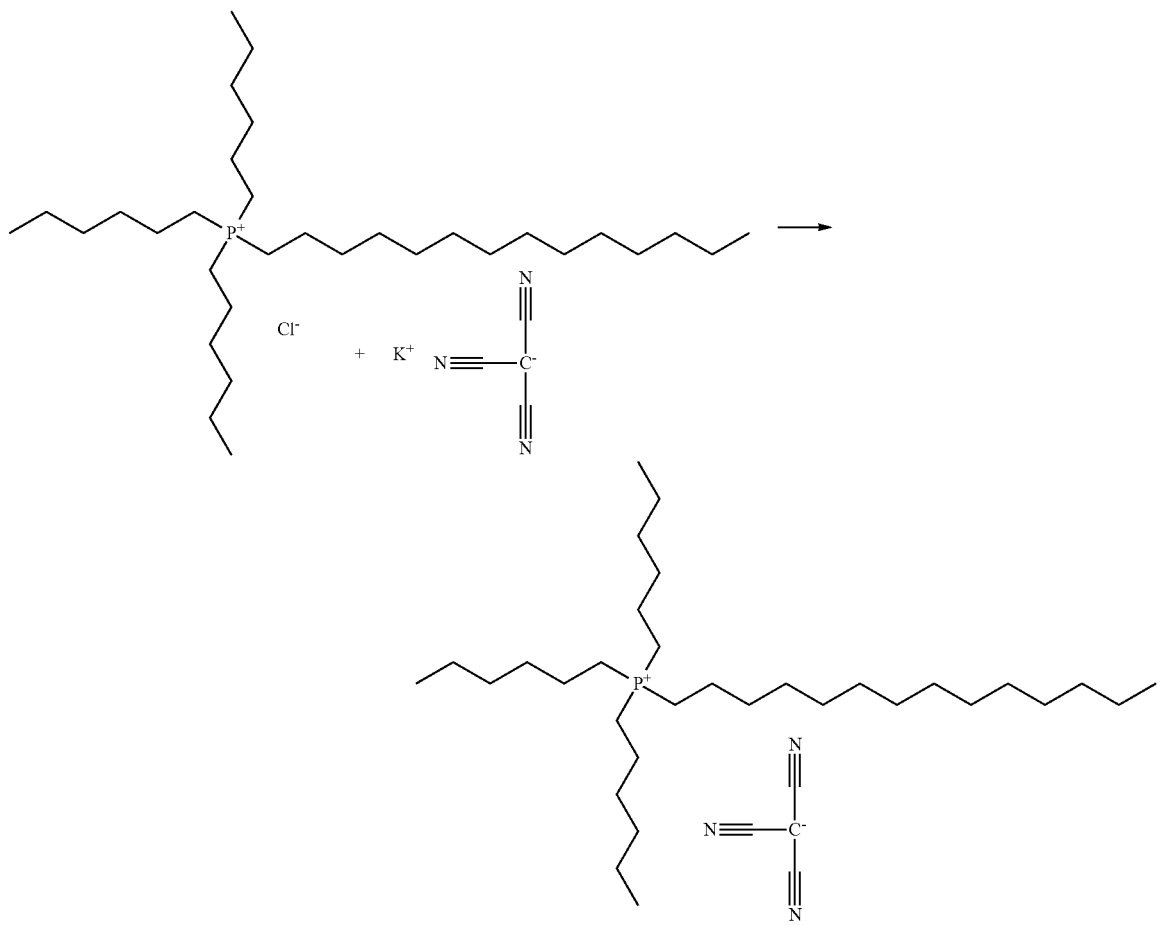

Analogously to Example A, 28 g of potassium tricyanomethide are added to 100 g of trihexyltetradecylphosphonium chloride, and the mixture is subjected to corresponding work-up.

1H NMR (d6-DMSO): δ=2.51 (m, 2H), 2.18 (m, 6H), 1.47 (m, 8H), 1.39 (m, 8H), 1.30 (m, 14H), 1.26 (m, 18H), 0.89 (m, 12H).

Example C

Synthesis of 1-methyl-1-octylpyrrolidinium tricyanomethide

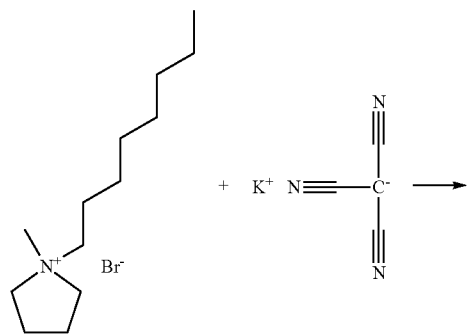

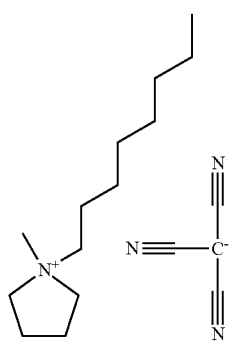

Analogously to Example A, 51 g of potassium tricyanomethide are added to 100 g of 1-methyl-1-octylpyrrolidinium bromide, and the mixture is subjected to corresponding work-up.

1H NMR (d6-DMSO): δ=3.20 (m, 4H), 3.05 (m, 4H), 2.74 (s, 3H), 1.84 (m, 2H), 1.45 (m, 2H), 1.05 (m, 10H), 0.63 (t, J(H,H)=6.6 Hz, 3H).

Example D

Synthesis of N-methyl-N-octylmorpholinium tricyanomethide

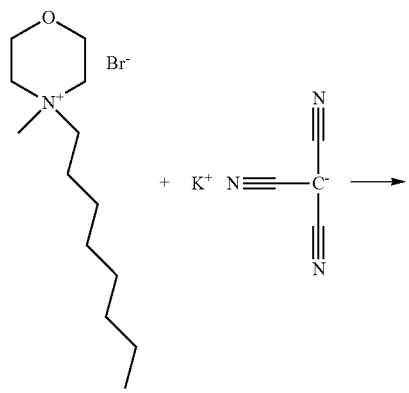

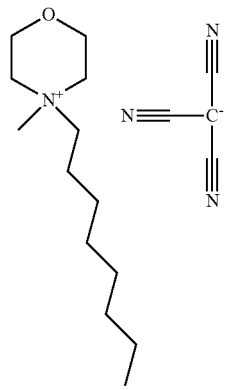

Analogously to Example A, 49 g of potassium tricyanomethide are added to 100 g of 4-methyl-4-octylmorpholinium bromide, and the mixture is subjected to corresponding work-up.

1H NMR (d6-DMSO): δ=3.67 (m, 4H), 3.15 (m, 4H), 2.88 (s, 3H), 2.71 (t, J(H,H)=2.0 Hz, 2H), 1.44 (m, 2H), 1.06 (m, 10H), 0.64 (t, J(H,H)=7.0 Hz, 3H).

Example E

Synthesis of 1-methyl-1-octylpiperidinium tricyanomethide

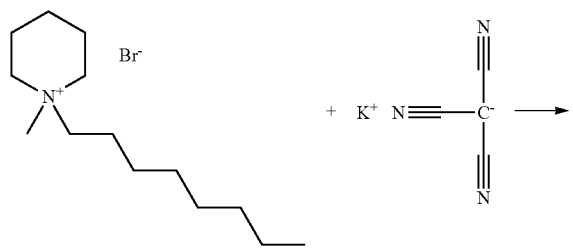

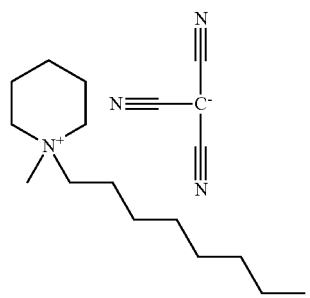

Analogously to Example A, 49 g of potassium tricyanomethide are added to 100 g of 1-methyl-1-octylpiperidinium bromide, and the mixture is subjected to corresponding work-up.

1H NMR (d6-DMSO): δ=3.33 (m, 4H), 3.28 (m, 6H), 2.99 (s, 3H), 2.50 (t, J(H,H)=2.0 Hz, 2H), 2.12 (m, 2H), 1.30 (m, 10H), 0.88 (t, J(H,H)=7.0 Hz, 3H).

Example F

Synthesis of 1-octyl-3-methylimidazolium tricyanomethide

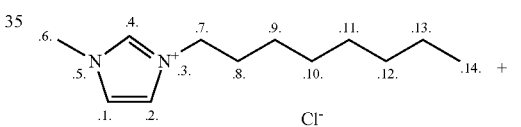

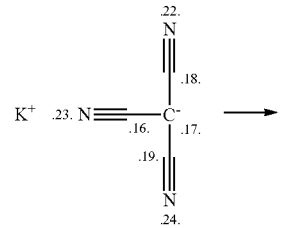

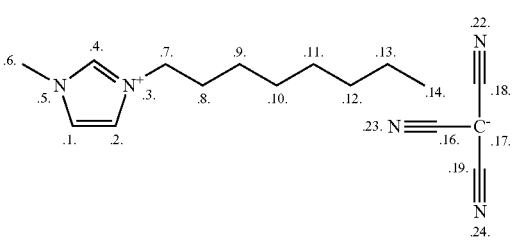

Analogously to Example A, 153 g of potassium tricyanomethide are added to 250 g of 3-methyl-1-octylimidazolium chloride, and the mixture is subjected to corresponding work-up.

1H NMR (d6-DMSO): δ=9.10 (s, 1H), 7.76 (t, J(H,H)=1.4 Hz, 1H), 7.70 (t, J(H,H)=1.4 Hz, 1H), 4.15 (t, J(H,H)=7.4 Hz, 2H), 3.85 (s, 3H), 1.25 (m, 12H), 0.86 (t, J(H,H)=6.6 Hz, 3H).

Example G

Synthesis of N-octylpyridinium tricyanomethide

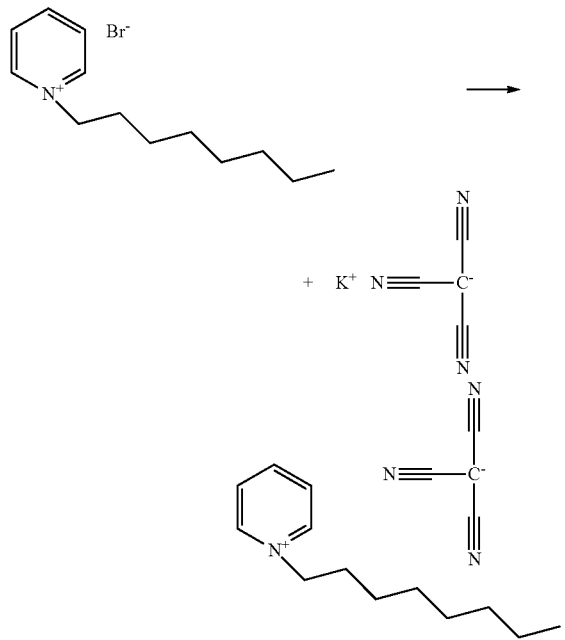

Analogously to Example A, 70 g of potassium tricyanomethide are added to 134 g of 1-octylpyridinium bromide, and the mixture is subjected to corresponding work-up.

1H NMR (d6-DMSO): δ=9.10 (d, J(H,H)=5.2 Hz, 2H), 8.61 (t, J(H,H)=8.7 Hz, 1H), 8.16 (t, J(H,H)=6.6 Hz, 2H), 4.60 (t, J(H,H)=8.5 Hz, 2H), 1.92 (m, 2H), 1.27 (m, 10H), 0.86 (t, J(H,H)=7.0 Hz, 3H).

Example 1

Procedure

Variant 1

The distribution coefficient is measured in double-walled glass vessels having a maximum volume of 10 ml. The initial concentration of butanol in the aqueous phase is 1% by weight. Equal weights (3 g) of each phase are brought into contact and mixed intensively by means of a magnetic stirrer (Variomag telesystem 06.07) at constant temperature (25° C.) for 24 h. The long experimental duration means that the achievement of equilibrium is ensured. The temperature control is carried out by means of a cryostat (Julabo F25 ME). After phase separation for 10 minutes, samples of each phase are taken and analysed.

The substance currently most investigated, oleyl alcohol, achieves a distribution coefficient of 3.4 and a selectivity of 208 in variant 1 of this investigation.

Procedure

Variant 2

0.9 g of ionic liquid is weighed out into a 2 ml plastic Eppendorf vessel. 0.9 g of 1% aqueous butanol solution is added. The solution is prepared immediately beforehand. The sample tubes are shaken in an Eppendorf Thermomixer Komfort at maximum speed at 25° C. for 24 h. They are then left to stand at 25° C. for 24 h in order to achieve good phase separation. The aqueous phase and the phase comprising the ionic liquid investigated in each case are separated and are each centrifuged again in an Eppendorf laboratory centrifuge at 14,500 rpm for 2 min. The butanol content in the two phases is determined by means of a GC Headspace from DMSO Matrix. The water content in the phase comprising the ionic liquid is determined by means of Karl Fischer titration. The ionic liquid content in the aqueous phase is determined by means of HPLC.

The following ionic liquids are investigated in variant 2:

[1] OMIM FAP (1-octyl-3-methylimidazolium tris(pentafluoroethyl)trifluorophosphate),
[2] OMIM PF6 (1-octyl-3-methylimidazolium hexafluorophosphate),
[3] OMIM NTF (1-octyl-3-methylimidazolium bis(trifluoromethylsulfonyl)-imide),
[4] OMIM BF4 (1-octyl-3-methylimidazolium tetrafluoroborate),
[5] OMIM TCB (1-octyl-3-methylimidazolium tetracyanoborate),
[6] OMIM TCM (1-octyl-3-methylimidazolium tricyanomethide),
[7] OMPL TCM (1-methyl-1-octylpyrrolidinium tricyanomethide),
[8] OMPI TCM (1-methyl-1-octylpiperidinium tricyanomethide),
[9] OMMO TCM (N-octyl-N-methylmorpholinium tricyanomethide),
[10] PH3T TCM (trihexyltetradecylphosphonium tricyanomethide),
[11] NH3T TCM (trihexyltetradecylammonium tricyanomethide).

The following table summarises the results: the average of two or three values is also listed in each case:

| Ionic liquid | $D_{Bu/IL}$ ([Bu]$_{IL}$/[Bu]$_{H2O}$) | $S(D_{Bu/IL}/D_{Bu/H2O})$ |
|---|---|---|
| OMIM FAP | 0.52 | 266 |
| OMIM PF6 | 0.92 | 55 |
| OMIM NTF | 1.51 | 135 |
| OMIM BF4 | 2.65 | 19 |
| OMIM TCB | 2.95 | 73 |
| OMIM TCM | 4.74 | 35 |
| OMPL TCM | 4.51 | 38 |
| OMPI TCM | 4.62 | 45 |
| OMMO TCM | 4.09 | 28 |
| PH3T TCM | 3.38 | 240 |
| NH3T TCM | 4.07 | 219 |
| Oleyl alcohol | 3.5 | 230 |

IL = abbreviation for ionic liquid,
Bu = abbreviation for butanol

Figure 3:
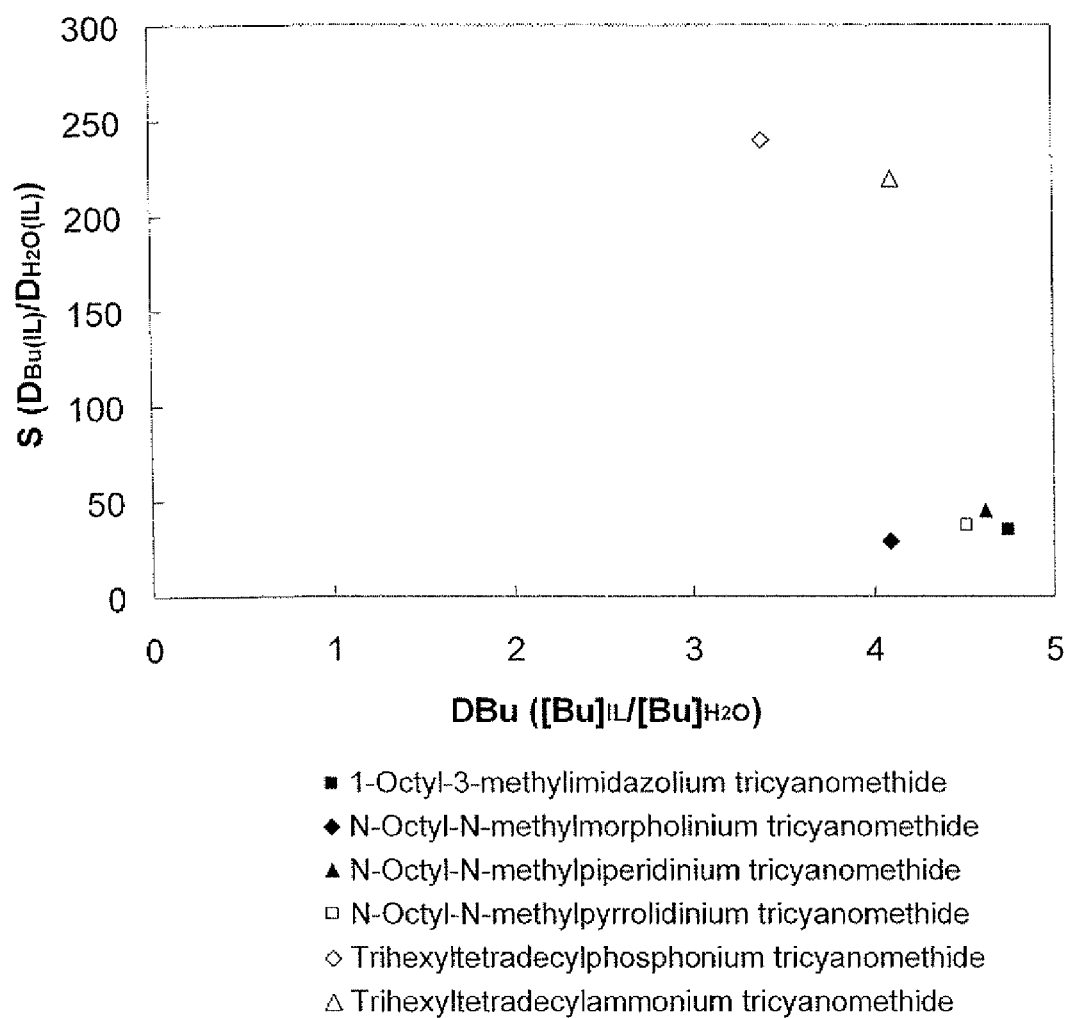

FIG. 3 summarises the results for the tricyanomethides in graph form.

FIG. 4 summarises the results for all measurement values.

The results show that ionic liquids containing TCM anions are highly suitable for the extraction of butanol from an aqueous solution.

The comparison shows that the ionic liquids containing tricyanomethide anions are alternatives to the use of ionic liquids containing tetracyanoborate anions, measured on OMIM TCB.

OMIM TOM exhibits the highest value of the distribution coefficient compared with the said ionic liquids.

Ammonium or phosphonium tricyanomethides, as described in the general part, are particularly suitable since they have both high selectivity and a high distribution coefficient.

LIST OF FIGURES

FIG. 1: Flow chart of a liquid-liquid extraction
FIG. 2: Flow chart of an extraction column for liquid-liquid extraction
FIG. 3: Graph of selectivity against distribution coefficient for ionic liquids containing a tricyanomethide anion for butanol
FIG. 4: Graph of selectivity against distribution coefficient for ionic liquids [1] to [11] for butanol

The invention claimed is:

1. Method for the liquid-liquid extraction of alcohols from aqueous solutions using at least one ionic liquid containing tricyanomethide anions as solvent.

2. Method according to claim 1, characterised in that the ionic liquid containing tricyanomethide anions forms at least one two-phase mixture with the aqueous solution comprising at least one alcohol.

3. Method according to claim 1, where
a) the aqueous solution comprising at least one alcohol is provided,
b) the aqueous solution from a) is mixed intensively with the at least one ionic liquid containing tricyanomethide anions, so that the ionic liquid is able to extract at least some of the alcohol from the aqueous solution and form an at least single-phase mixture with this alcohol,
c) the at least single-phase mixture from b) is separated off from the aqueous solution,
d) the single-phase mixture from b) is separated into the components alcohol and ionic liquid, and optionally
e) the ionic liquid from d) is fed back into step b).

4. Method according to claim 1, characterised in that the method is carried out continuously or semi-continuously.

5. Method according to claim 1, characterised in that the at least one alcohol is selected from the group ethanol, isopropanol, propanol, n-butanol or isomers of n-butanol, or mixtures thereof.

6. Method according to claim 5, characterised in that the at least one alcohol is n-butanol.

7. Method according to claim 1, characterised in that the aqueous solution comprising at least one alcohol is a fermentation broth.

8. Method according to claim 1, characterised in that the fermentation broth originates from an acetone-butanol-ethanol fermentation.

9. Method according to claim 1 characterised in that the at least one ionic liquid containing tricyanomethide anions is selected from the group of the compounds of the formula (1), (2) or (3):

where
R in each case, independently of one another, denotes
a straight-chain or branched alkyl having 1-20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 5-7 C atoms, which may be substituted by alkyl groups having 1-6 C atoms,
with the proviso that at least two substituents R have at least 5 C atoms.

10. Method according to claim 1, characterised in that the at least one ionic liquid containing tricyanomethide anions is selected from the group of the compounds of the formula (4) or (5):

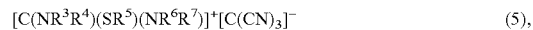

where
$R^3$ to $R^7$ each, independently of one another, denote
H, where H is excluded for $R^5$,
a straight-chain or branched alkyl having 1 to 20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 3-7 C atoms, which may be substituted by alkyl groups having 1-6 C atoms.

11. Method according to claim 1, characterised in that the at least one ionic liquid containing tricyanomethide anions is selected from the group of the compounds of the formula (6)

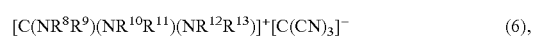

where
$R^8$ to $R^{13}$ each, independently of one another, denote
H,
a straight-chain or branched alkyl having 1 to 20 C atoms,
a straight-chain or breathed alkenyl having 2-20 C atoms and one or more double bonds,
a straight-chain or branched alkynyl having 2-20 C atoms and one or more triple bonds,
saturated, partially or fully unsaturated cycloalkyl having 3-7 C atoms, which may be substituted by alkyl groups having 1-6 C atoms.

12. Method according to claim 1, characterised in that the at least one ionic liquid containing tricyanomethide anions is selected from the group of the compounds of the formula (7)

where
$HetN^{z+}$ denotes a heterocyclic cation selected from the group

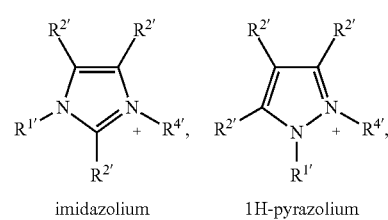

imidazolium    1H-pyrazolium

-continued

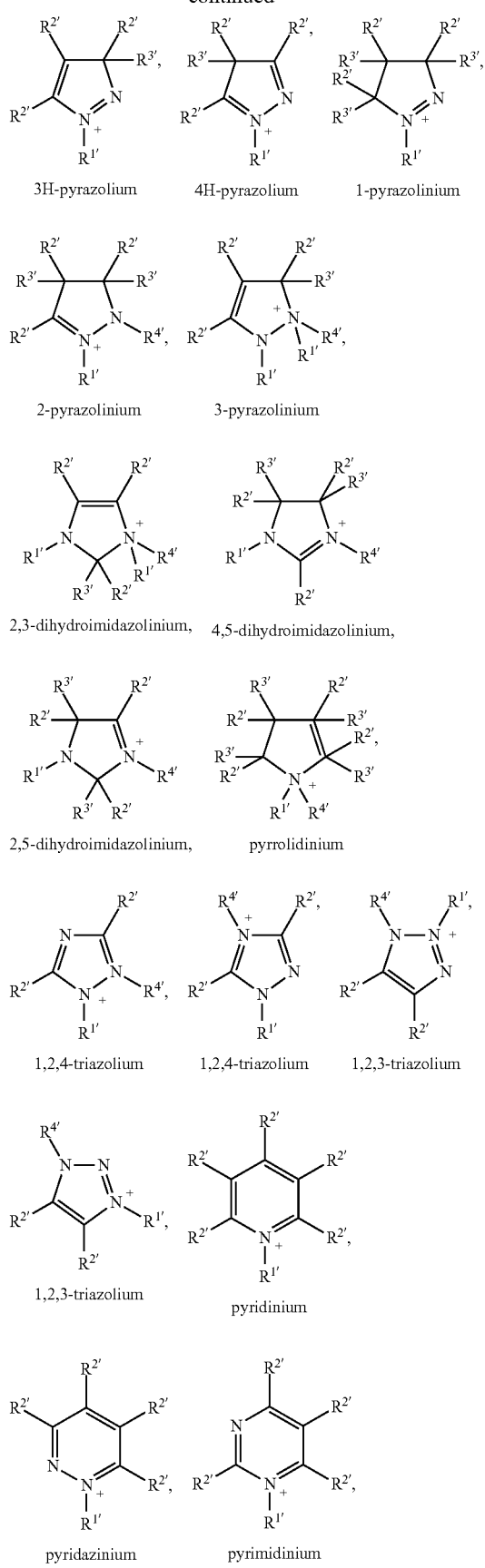

3H-pyrazolium, 4H-pyrazolium, 1-pyrazolinium 2-pyrazolinium, 3-pyrazolinium 2,3-dihydroimidazolinium, 4,5-dihydroimidazolinium, 2,5-dihydroimidazolinium, pyrrolidinium 1,2,4-triazolium, 1,2,4-triazolium, 1,2,3-triazolium 1,2,3-triazolium, pyridinium pyridazinium, pyrimidinium -continued

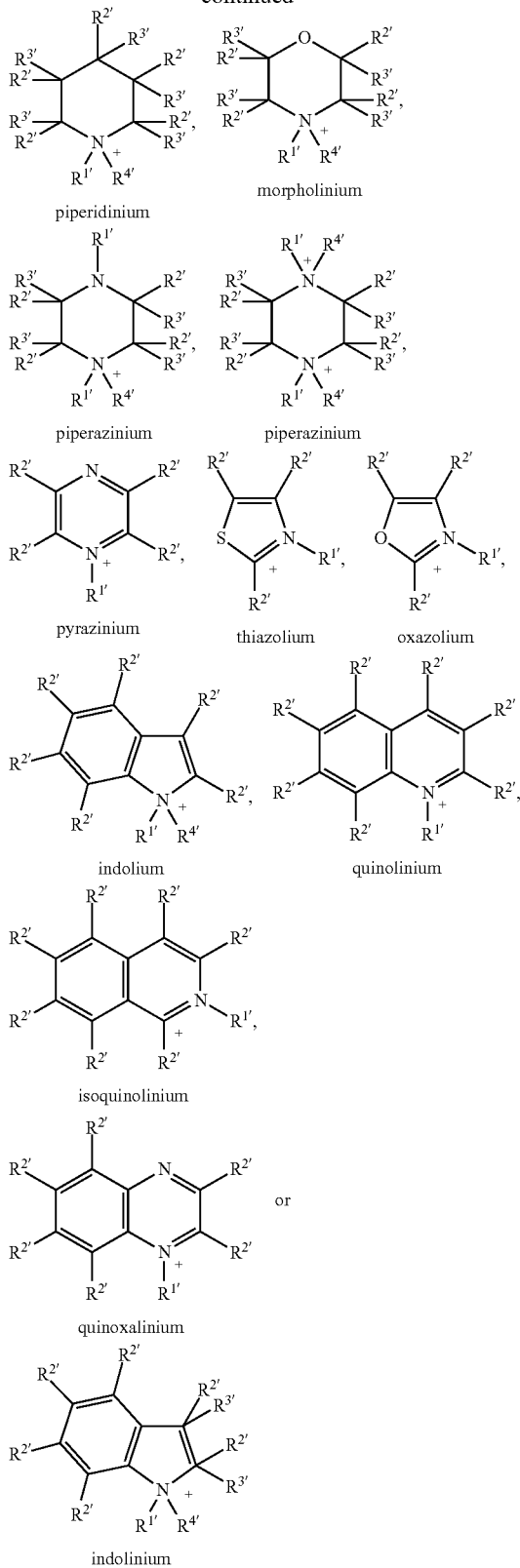

piperidinium, morpholinium piperazinium, piperazinium pyrazinium, thiazolium, oxazolium indolium, quinolinium isoquinolinium quinoxalinium or indolinium where the substituents
R$^{1'}$ to R$^{4'}$ each, independently of one another, denote
a straight-chain or branched alkyl having 1-20 C atoms, a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 5-7 C atoms, which may be substituted by alkyl groups having 1-6 C atoms,
where the substituents $R^{1'}$, $R^{2'}$, $R^{3'}$ and/or $R^{4'}$ together may also form a ring system.

13. Method according to claim 1, characterised in that the at least one ionic liquid containing tricyanomethide anions is selected from the group of the compounds of the formulae (1), (2), and (7):

  (1),

  (2),

  (7), where
R in each case, independently of one another, denotes
a straight-chain or branched alkyl having 1-20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 5-7 C atoms, which may be substituted by alkyl groups having 1-6 C atoms,
with the proviso that at least two substituents R have at least 5 C atoms;
$HetN^{z+}$ denotes a heterocyclic cation selected from the group

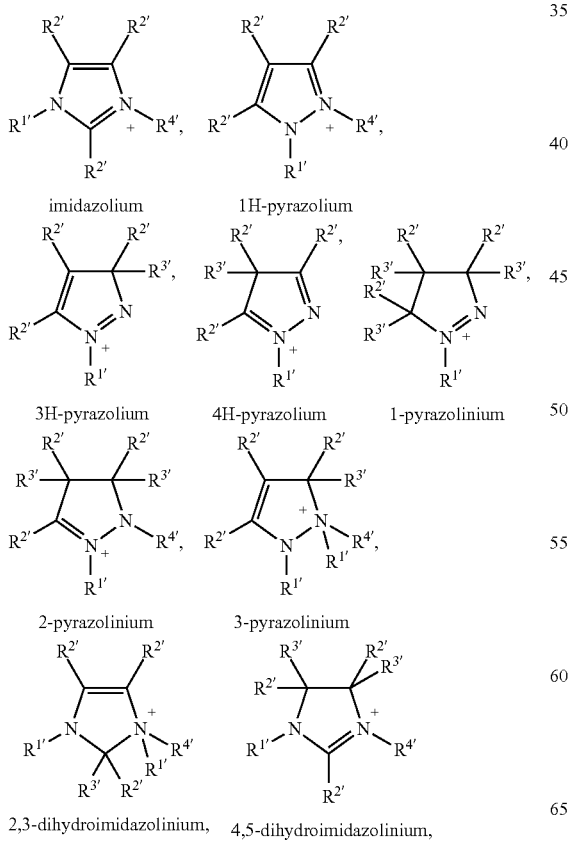

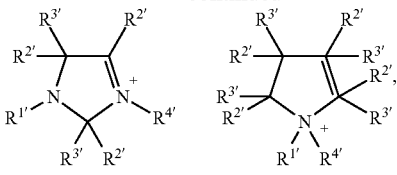

2,5-dihydroimidazolinium,  pyrrolidinium

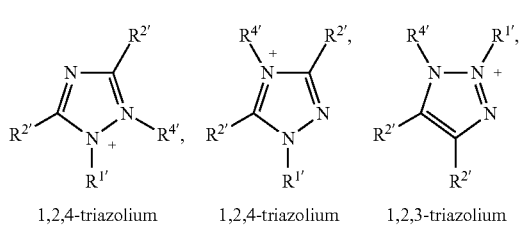

1,2,4-triazolium  1,2,4-triazolium  1,2,3-triazolium

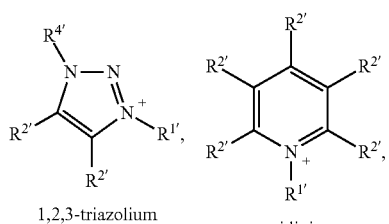

1,2,3-triazolium  pyridinium

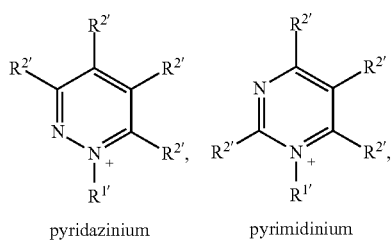

pyridazinium  pyrimidinium

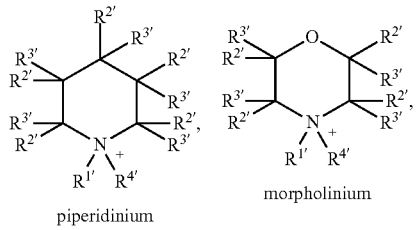

piperidinium  morpholinium

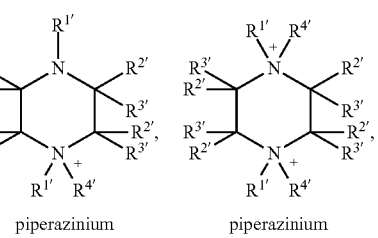

piperazinium  piperazinium

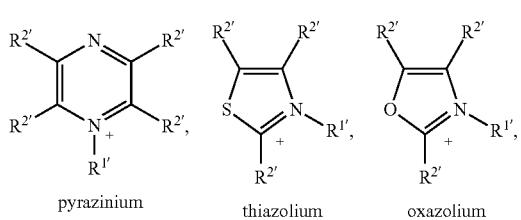

pyrazinium  thiazolium  oxazolium

-continued

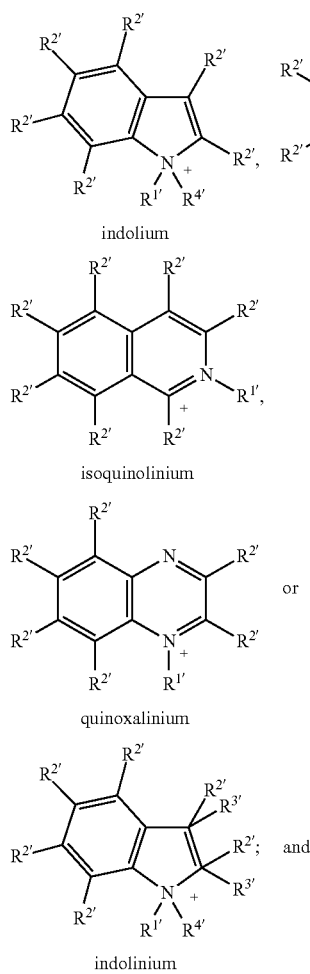

indolium quinolinium isoquinolinium quinoxalinium or indolinium; and

R$^{1'}$ to R$^{4'}$ each, independently of one another, denote
a straight-chain or branched alkyl having 1-20 C atoms,
a straight-chain or branched alkenyl having 2-20 C atoms and one or more double bonds,
a straight-chain or branched alkenyl having 2-20 C atoms and one or more triple bonds,
saturated, partially or fully unsaturated cycloalkyl having 5-7 C atoms, which may be substituted by alkyl groups having 1-6 C atoms,
where the substituents R$^{1'}$, R$^{2'}$, R$^{3'}$ and/or R$^{4'}$ together may also form a ring system.

14. Method according to claim 1, characterised in that the at least one ionic liquid containing tricyanomethide anions is selected from the group
1-octyl-3-methylimidazolium tricyanomethide,
1-decyl-3-methylimidazolium tricyanomethide,
1-dodecyl-3-methylimidazolium tricyanomethide,
trihexyltetradecylammonium tricyanomethide,
trihexyltetradecylphosphonium tricyanomethide,
N-octylpyridinium tricyanomethide,
1-octyl-1-methylpyrrolidinium tricyanomethide,
N-octyl-N-methylmorpholinium tricyanomethide,
1-octyl-1-methylpiperidinium tricyanomethide.

15. A method of liquid-liquid extraction of alcohols from aqueous solutions, comprising:
a) providing an aqueous solution containing at least one alcohol,
b) the aqueous solution from a) is mixed intensively with the at least one ionic liquid containing tricyanomethide anions, so that the ionic liquid is able to extract at least some of the alcohol from the aqueous solution and form an at least single-phase mixture with this alcohol,
c) separating said at least single-phase mixture from the aqueous solution,
d) separating said single-phase mixture from b) into the components alcohol and ionic liquid, and optionally
e) feeding the ionic liquid from d) back into step b).

* * * * *

UNITED STATES PATENT AND TRADEMARK OFFICE
CERTIFICATE OF CORRECTION

PATENT NO. : 8,440,869 B2
APPLICATION NO. : 13/001857
DATED : May 14, 2013
INVENTOR(S) : Pitner et al.

Page 1 of 1

It is certified that error appears in the above-identified patent and that said Letters Patent is hereby corrected as shown below:

In the Claims

Column 24, Line 40, Claim 11 reads: "a straight-chain or breathed alkenyl having 2-20 C atoms"
should read -- a straight-chain or branched alkenyl having 2-20 C atoms --.

Signed and Sealed this
Twenty-second Day of October, 2013

Teresa Stanek Rea
*Deputy Director of the United States Patent and Trademark Office*